United States Patent [19]

Hattori et al.

[11] Patent Number: 5,578,065
[45] Date of Patent: Nov. 26, 1996

[54] LOW-FREQUENCY THERAPEUTIC DEVICE HAVING A FLEXIBLE ADHESIVE SHEET ELECTRODE

[75] Inventors: Hidenori Hattori; Naoto Takizawa; Hidenori Hadate; Tomoko Kondou, all of Tosu, Japan

[73] Assignee: Hisamitsu Pharmaceutical Co., Inc., Saga, Japan

[21] Appl. No.: 244,512

[22] PCT Filed: Dec. 4, 1992

[86] PCT No.: PCT/JP92/01590

§ 371 Date: May 31, 1994

§ 102(e) Date: May 31, 1994

[87] PCT Pub. No.: WO93/10855

PCT Pub. Date: Jun. 10, 1993

[30] Foreign Application Priority Data

Dec. 6, 1991 [JP] Japan .................. 3-100812 U

[51] Int. Cl.$^6$ ........................................ A61N 1/32
[52] U.S. Cl. .................. 607/46; 607/72; 607/115; 607/149
[58] Field of Search ................. 607/46, 48, 50, 607/72, 115, 142, 148, 149

[56] References Cited

U.S. PATENT DOCUMENTS

| | | | |
|---|---|---|---|
| 4,398,545 | 8/1983 | Wilson | 607/46 X |
| 4,922,906 | 5/1990 | Takeuchi et al. | 607/72 |
| 4,949,721 | 8/1990 | Tosiu et al. | 607/46 |
| 4,982,742 | 1/1991 | Claude | 607/50 |

FOREIGN PATENT DOCUMENTS

| | | | |
|---|---|---|---|
| 2646779 | 11/1990 | France | 607/46 |
| 63-188042 | 12/1988 | Japan . | |
| 1-221174 | 9/1989 | Japan . | |
| 2-49549 | 4/1990 | Japan . | |
| 3-5445 | 1/1991 | Japan . | |
| 3-182264 | 8/1991 | Japan . | |
| 3-236860 | 10/1991 | Japan . | |

Primary Examiner—William E. Kamm
Assistant Examiner—Jeffrey R. Jastrzab
Attorney, Agent, or Firm—Jordan and Hamburg

[57] ABSTRACT

A low-frequency therapeutic device of a compact type which effectively carries out a comfortable and effective treatment, which does not require a user to find sweet or effective spots and which can be operated easily. The therapeutic device includes a therapeutic main body with a built-in low-frequency pulse output devices, a power supply fitted to the main body, a flexible sheet electrode having an area greater than that of the bottom surface of the therapeutic device main body, and an adhesive pad spread on the sheet electrode.

15 Claims, 16 Drawing Sheets

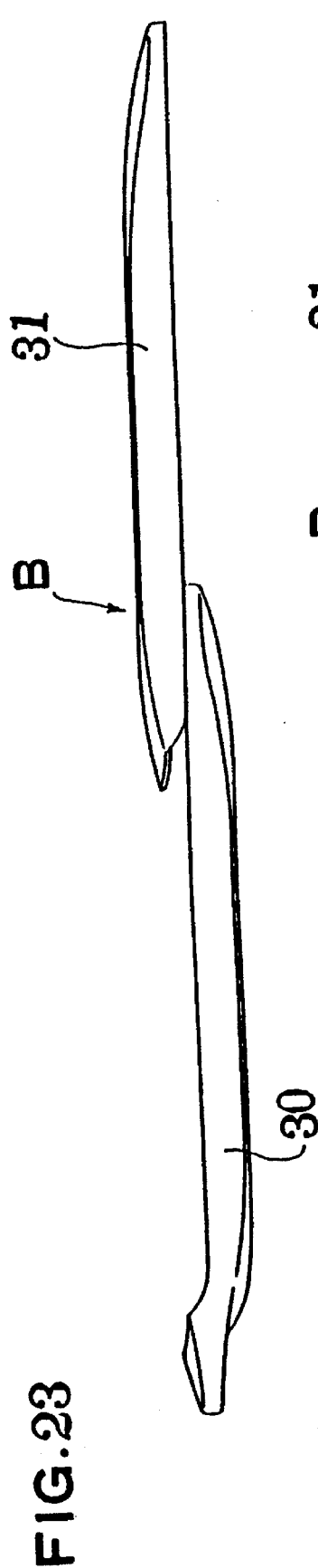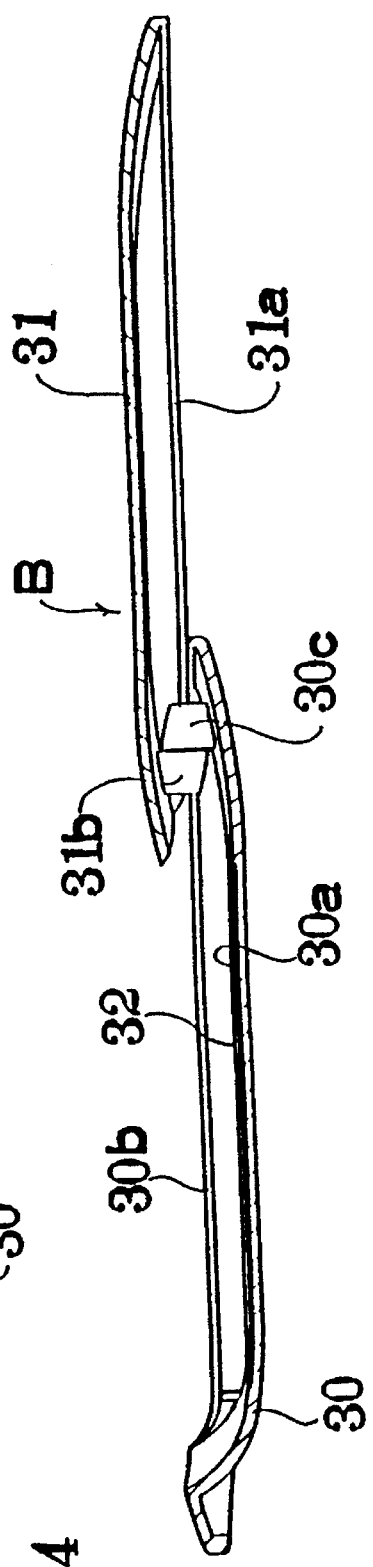
FIG. 23
FIG. 24

LOW-FREQUENCY THERAPEUTIC DEVICE HAVING A FLEXIBLE ADHESIVE SHEET ELECTRODE

BACKGROUND OF THE INVENTION

This invention relates to a low-frequency therapeutic device having a flexible adhesive sheet electrode (which is firmly adhered to the skin of a human body) which can stimulate nerves, activate muscular movement and promote blood circulation so as to ease various symptoms such as stiffness, pain paralysis, and fatigue by giving a low-frequency current having the same properties as those of a bioelectric current which flows inside the human body, to the inside of the human body by way of the skin.

Conventionally, there is known a low-frequency therapeutic device which is used in such a manner that a pair of electrodes are adhered onto the surface of the human skin and a high voltage pulse having a low frequency is applied between the electrodes so that an electric stimulus is given to the human body to apply a therapeutic effect.

This type of low-frequency therapeutic device comprises therapeutic elements which are adhered to the human body, and a controller for controlling the operation of therapeutic elements. These therapeutic elements and the controller, however, must be connected to each other by means of cords can and these cords bother a user of the device.

In view of the above, a low-frequency therapeutic device which is of a cordless type and is light-weight has been developed as described in Japanese Utility Model Laid-open No. HEI 3-5445, wherein the therapeutic device attaches adhesive conductors or electrodes to the bottom surface of a therapeutic main body incorporating a power source therein.

Although the therapeutic device described in the above publication has succeeded in making cords unnecessary and in acquiring light-weightedness, the size of the adhesive conductors are arranged corresponding to the size of the bottom surface of the therapeutic device. Accordingly, since the main body of the therapeutic device has an extremely poor flexibility, it is extremely difficult to adhere the adhesive conductors to the parts of the human skin which constantly move resulting in poor adhering of the adhesive conductors (for example, parts such as the shoulders or neck which vigorously move).

The smaller the main body of the therapeutic device becomes, the greater the above-mentioned problem. Furthermore, since the area of each adhesive conductor is small, the contact resistance between the adhesive conductor and the parts of the human skin increases, whereby a user feels a discomfort with pricking pains.

The above discomfort is brought to the user in a mechanism, wherein in the low-frequency therapy, in case a pair of electrodes which are made of adhesive conductors are placed on effective spots of the human body respectively, an electric current flows inside the human body so that a comfortable and effective therapy can be achieved, while in case a pair of electrodes are not placed on the effective spots respectively, when an output of electric pulse in generated, the electric current flows along the surface of the human skin without flowing inside the human body and give a discomfort to the user.

Furthermore, the conventional low-frequency therapeutic device is capable of operating in several modes such as tapping, massaging and vibrating upon varying the period of electric pulse generated. To obtain a desired mode or stimulus, however, the user must operate a mode selection switch each time he wants to change and obtain the desired mode, such an operation is cumbersome.

Furthermore, since the low-frequency therapeutic device is not provided with a case which can readily store the therapeutic device in a compact form, the carrying thereof is inconvenient.

Accordingly, it is an object of the present invention to provide a low-frequency therapeutic device which can overcome the above-mentioned defects.

SUMMARY OF THE INVENTION

This invention discloses a low-frequency therapeutic device having a flexible adhesive sheet electrode comprising a therapeutic device main body with built-in low-frequency pulse output means, a power supply fitted to the main body, a flexible sheet electrode having an area greater than that of the bottom surface of the therapeutic device main body, and an adhesive pad spread on the sheet electrode.

This invention is also characterized in that the sheet electrode is replaceably mounted on the therapeutic device, that the adhesive pad is replaceably spread on the sheet electrode, that plurality of modes which are different in periods of generating low-frequency electric pulse are programmed in a control unit provided at the low-frequency pulse output means and these modes are output continuously and in sequence by a single switching operation, and that the sheet electrode is mounted on the therapeutic device and the adhesive pad is spread on the sheet electrode and the sheet electrode is stored in a therapeutic device storing case provided with a sheet electrode adhering surface inside thereof in such a manner that the sheet electrode is adhered to the sheet electrode adhering surface by way of the adhering pad.

In carrying out therapy using the low-frequency therapeutic device according to this invention, the sheet electrode mounted on the therapeutic device main body is adhered to an affected part of a user by way of the adhesive pad and low-frequency electric pulses are generated by the low-frequency pulse output means built in the therapeutic device main body and the electric pulses are applied to the user by way of the sheet electrodes so as to give a stimulus to nerves of the affected part of the user.

In the above therapy, since the sheet electrode is made of a flexible sheet and has an area greater than that of the bottom surface of the therapeutic device main body, the sheet electrode can be completely adhered to the parts of human body skin which constantly move, such as the shoulders or neck which vigorously move.

Furthermore, since the sheet electrode has an area greater than that of the bottom surface of the therapeutic device main body and therefore can assure a large conductive surface, the sheet electrode can easily cover a plurality of effective spots. Accordingly, without being bothered by finding the positions of the effective spots, by merely adhering the sheet electrode to a stiffened part of the human body, a comfortable and effective therapy is realized avoiding the pricking or biting pains caused at the time of generating electric pulses which give the user discomfort.

Furthermore, since the therapeutic device main body, the sheet electrode and the adhesive pad are replaceably mounted from each other, only a malfunctioning or defective part or component can be picked up and replaced with a new one so that the device can be repaired in an inexpensive manner while assuring a favorable therapeutic functions.

Especially, as the adhesive pads lose their adhesiveness since they have to be adhered or peeled off repetitiously, such an adhesive pad can be replaced a new one so that the complete adhering of the therapeutic device to human body skin can be favorably assured.

A plurality of modes which differ in periods of generated low-frequency electric pulse including a mode giving a user a feeling of heavy tapping, a mode giving a user a feeling of vibration with varying strength, a mode giving a user a feeling of rhythmical tapping, and a mode giving a user a feeling of massaging can be programmed in the control unit and these modes can be output continuously and in sequence and, when the predetermined operating time is over, the therapeutic device can stop automatically. In this manner, various stimuli can be given to nerves which tend to get along a single monotonous stimulus giving rise to an effective therapy.

Furthermore, once the operating switch is turned on, these modes are automatically carried out giving various stimuli peculiar to the respective modes to the affected part of the users activating the muscular movements promoting the circulation of blood and easing various symptoms such as stiffness, pains, paralysis and fatigue, thus enhancing the therapeutic effect and the manipulation or handling of the low-frequency therapeutic device is facilitated.

DESCRIPTION OF THE DRAWINGS

FIG. 23 is a right-side elevational view of the therapeutic device storing case in a lid-opened condition.

FIG. 24 is a cross-sectional view of the therapeutic device storing case taken along a line V—V of FIG. 22.

DESCRIPTION OF THE INVENTION

The present invention is explained in view of the drawings.

In FIGS. 1 to 7, indicates a low-frequency therapeutic device and the low-frequency therapeutic device A is constructed such that a therapeutic device main body 1, a sheet electrode 2 and an adhesive pad 3 are replaceably mounted on each other and the low-frequency therapeutic device can be stored in a low-frequency therapeutic device storing case B, as shown in FIGS. 14–24. The components are explained respectively hereinafter.

[Therapeutic Device Main Body]

Figure 1:
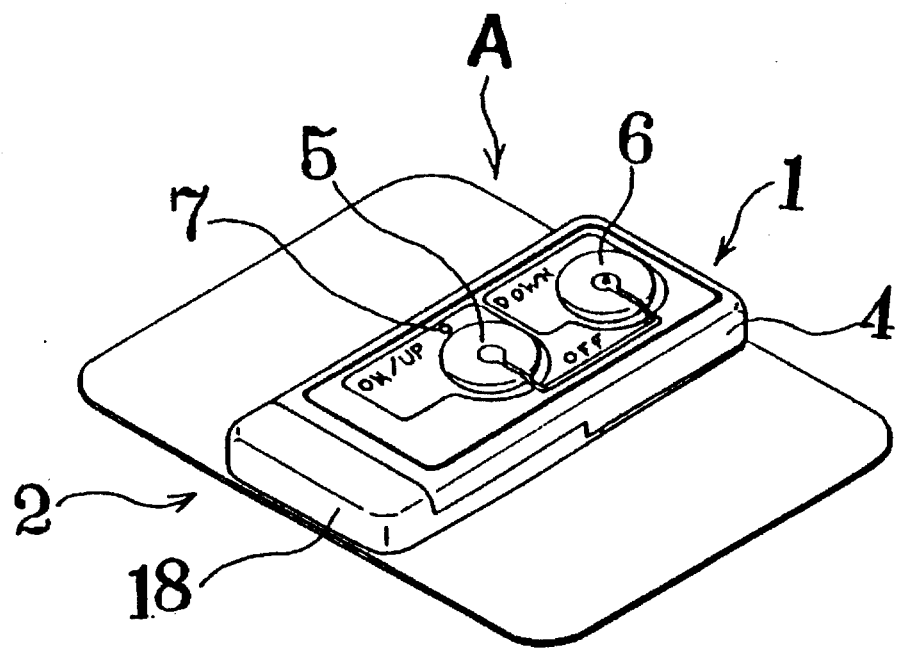
FIG. 1 is a perspective view of a low-frequency therapeutic device according to this invention showing an upper portion thereof.
Figure 2:
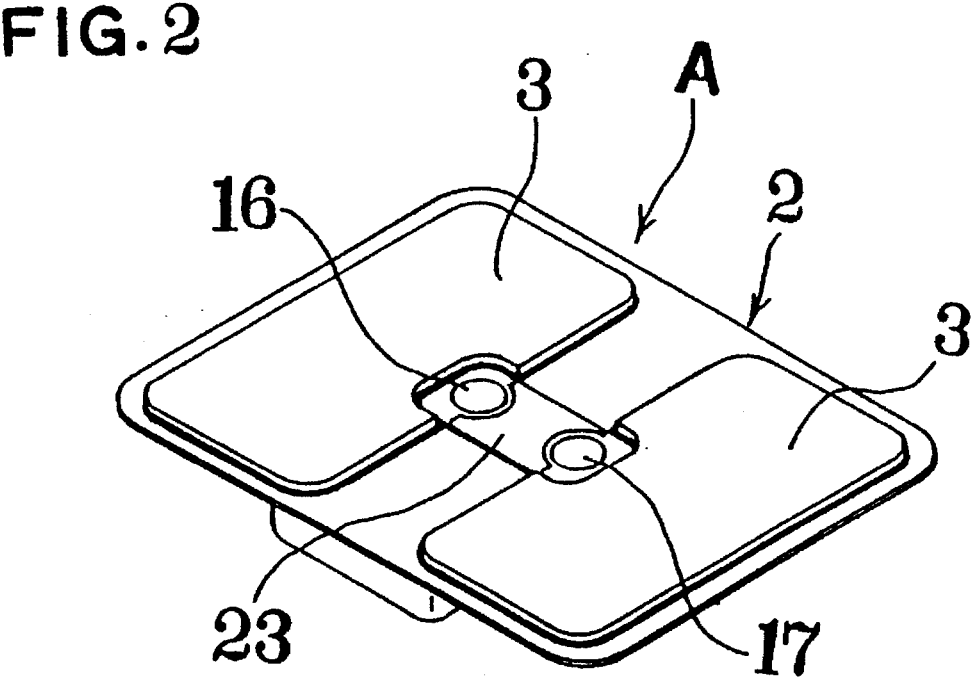
FIG. 2 is a perspective view of the low-frequency therapeutic device showing a lower portion thereof.
Figure 3:
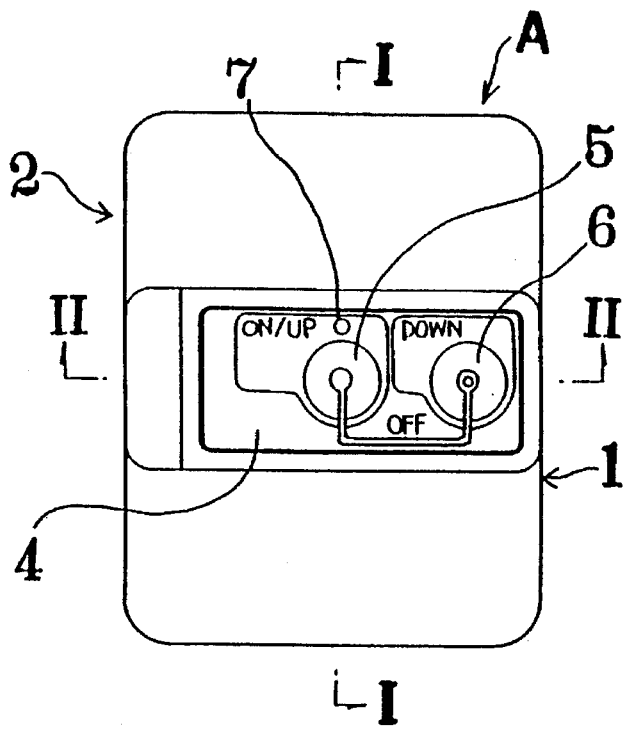
FIG. 3 is a plan view of the low-frequency therapeutic device.
Figure 8:
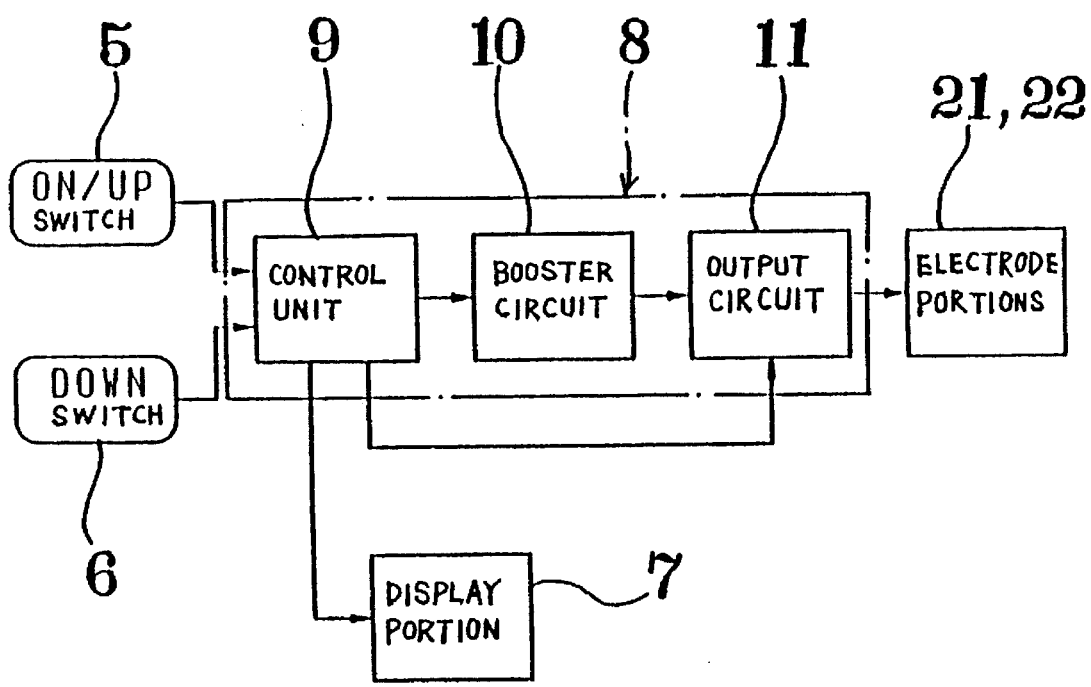
FIG. 8 is a block diagram of a low-frequency pulse output means.
Figure 9:
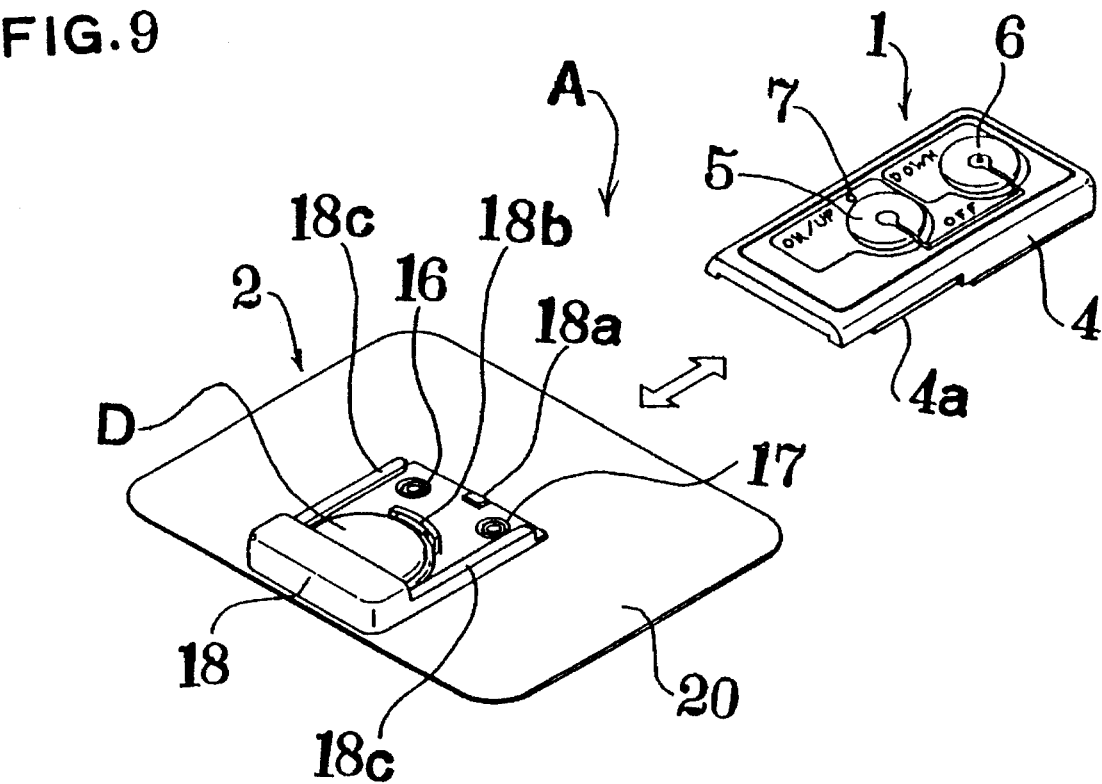
FIG. 9 is an exploded view of the low-frequency therapeutic device.

Therapeutic device main body 1, as shown in FIGS. 1, 3 and 9, is provided with an ON/UP switch 5, a DOWN switch 6 and a display portion 7 on the surface of a main body case 4, while the therapeutic device main body 1 encases a low-frequency pulse output means 8 in the main body case 4. The output means 8, as shown in FIG. 8, comprises a control unit 9 which connects the above-mentioned ON/UP switch 5 and the DOWN switch 6 to an input port thereof while connecting the display portion 7 to an output port thereof, and a booster circuit 10 and an output circuit 11 are connected to the output port of the control unit 9. A pair of electrode portions 21, 22 of the sheet electrode 2, which are described later, are connected to the output circuit 11.

In this embodiment, the ON/UP switch 5 is made of a membrane switch. The ON/UP switch 5 transmits an ON signal (an output signal) to the control unit 9 when a basic clock in the control unit is stopped, while the basic clock is operated, the ON/UP switch 5 can transmit an UP signal (output amplifying signal) to the control unit 9.

The DOWN switch 6 is made of a membrane switch and can transmit a DOWN signal (output reducing signal) to the control unit 9.

The control unit 9, upon receiving an ON signal from the ON/UP switch 5, starts transmission of basic clocks and thereafter starts transmission of a booster pulse and a gate pulse to the booster circuit 10 and the output circuit 11 respectively. Furthermore, the control unit 9, upon receiving an UP signal, increases the number of booster pulses to be generated until the gate pulse is generated.

On the other hand, upon receiving a DOWN signal, the control unit 9 decreases the number of booster pulses to be generated.

The control unit 9 accepts the UP signals the predetermined times (for example 5 to 15), while the control unit 9 accepts the DOWN signals the same times as that of the UP signals.

When the control unit 9 accepts the UP signal and the DOWN signal simultaneously or accepts the DOWN signals at the same times as those of the UP signals, the control unit 9 stops the transmission of a basic clock and all the outputs are stopped.

Furthermore, when a predetermined time (for example, 5 to 30 minutes) lapses, a timer provided in the control unit 9 is operated so as to stop transmission of signals.

The display portion 7 flickers an LED corresponding to the output pulse.

The booster circuit 10 has an inductance to carry out a switching operation on the booster pulse, so that a counter electromotive force from the inductance charges a condenser.

Accordingly, as the time or number of booster pulses increases, a final output voltage is increased.

The output circuit 11, upon receiving a gate signal, discharges its electric charge in the condenser of the booster circuit 10 and transmits an output pulse to the sheet electrode 2.

Accordingly, the output frequency is determined by an interval of gate pulses.

As mentioned above, a program is stored in the control unit 9 of the low-frequency pulse output means 8 in such a manner that corresponding to the output pulse transmitted from the output circuit 11, seven types of stimulating modes which will be described later can be applied to an affected part of a user, and the user operates the ON/UP switch 5 so as to output respective modes in a predetermined interval continuously. Namely, when the ON/UP switch 5 is turned on, ① a tapping mode which gives rise to a heavy tapping feeling is continued for a few minutes,
② a vibrating mode which gives rise to a vibrating feeling with a strength changing function is continued for a few minutes,
③ a continuous tapping mode which gives rises to a light and fast tapping feeling is continued for a few minutes,
④ a massaging mode which gives rise to a massaging effect is continued for a few minutes,
⑤ a light massaging mode which gives rise to a light massaging effect is continued for a few minutes,
⑥ a massaging mode which gives rise to a massaging effect is continued for a few minutes, and
⑦ an ordinary tapping mode which gives rise to a tapping feeling of ordinary strength is continued for a few minutes, and finally the timer incorporated in the control unit 9 is operated so as to automatically stop the generation of output.

Besides stopping the supply of electric current when the above-mentioned predetermined time (for example, 15 to 30 minutes) elapses, the low-frequency pulse output means 8 adopts the following safety precaution. When trouble occurs in the clock circuit or the output circuit 11, the counter electromagnetic force generated by applying pulses to inductance and stored as charged in the condenser, is discharged, whereby the output is stopped and a human body is protected.

Furthermore, since the capacity of the inductance and condenser is restricted, the maximum output current is regulated accordingly, and does not exceed a limit current of 20 mA.

Still furthermore, at the time of starting an operation of the device, the output is increased step by step by pushing the ON/UP switch 5 every time from the weakest output level, so that the body of the user is protected from surging stimuli.

Figure 5:
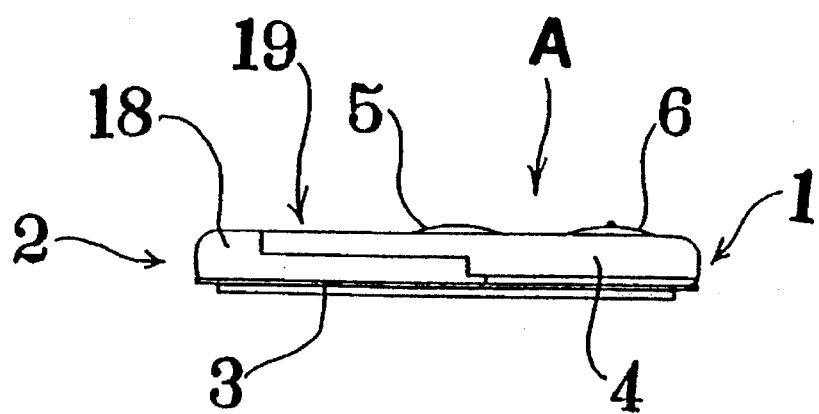
FIG. 5 is a front elevational view of the low-frequency therapeutic device.
Figure 6:
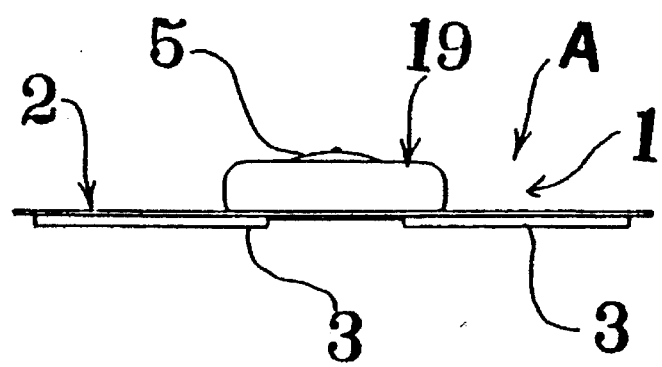
FIG. 6 is a left-side elevational view of the low-frequency therapeutic device.
Figure 7:
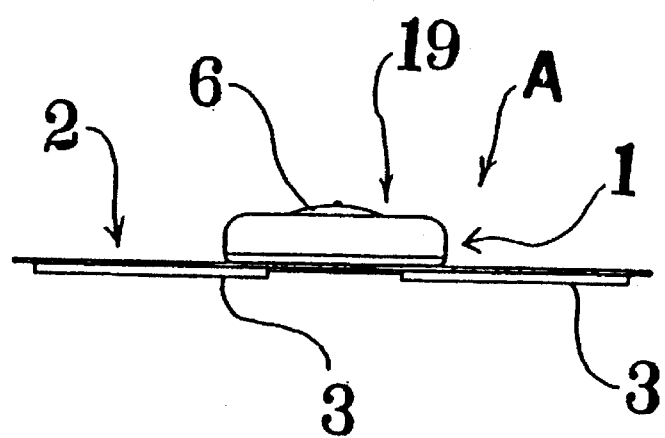
FIG. 7 is a right-side elevational view of the low-frequency therapeutic device.
Figure 10:
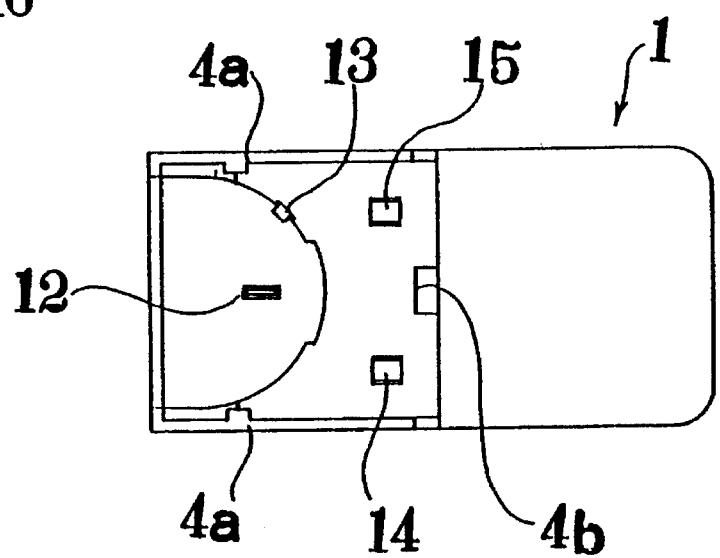
FIG. 10 is a bottom view of the therapeutic device main body.

The main body case 4, as shown in FIGS. 9 and 10, is replaceably and slidably mounted on a battery case 18 provided with a pair of sheet electrodes 2 as will be explained hereinafter. A therapeutic device case 19 having a flattened rectangular shape is formed by a combination of these cases 4 and 18 as shown in FIGS. 5 to 7.

Figure 11:
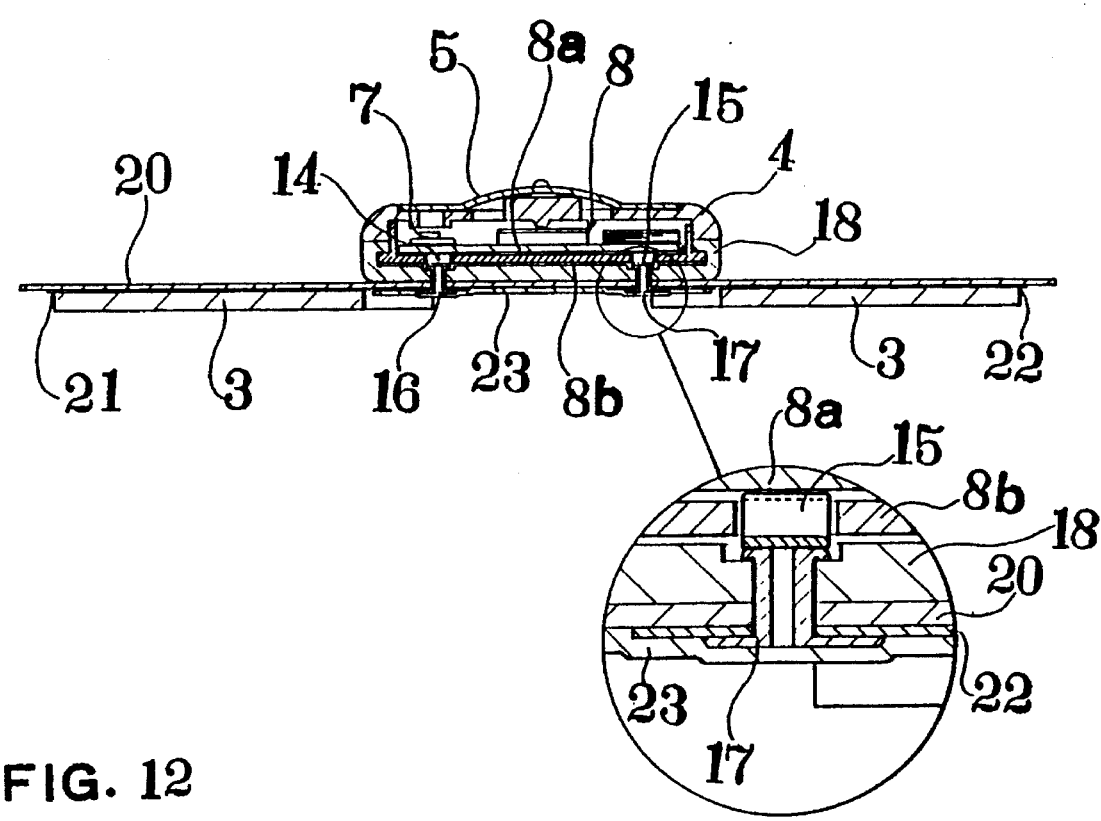
FIG. 11 is a cross-sectional view of the low-frequency therapeutic device taken along a line I—I of FIG. 3.
Figure 12:
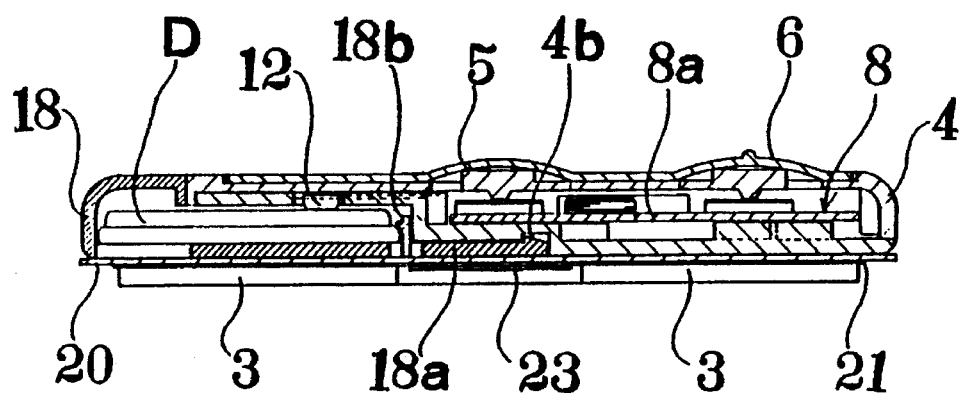
FIG. 12 is a cross-sectional view of the low-frequency therapeutic device taken along a line II—II of FIG. 3.

As shown in FIGS. 10 to 12, the main body case 4 is provided with battery connecting fittings 12, 13 and output terminals 14, 15 on an inner wall thereof.

These battery connecting fittings 12, 13 come into contact with positive and negative electrodes of the battery D as a power supply source mounted on the sheet electrode 2 so as to supply electricity to the low-frequency pulse generating means 8. The input terminals 16, 17 mounted on the sheet electrode 2 come into contact with the respective output terminals 14, 15. Numeral 4a indicates slide engaging members provided at the front and rear peripheries of the main body case 4, numeral 4b indicates engaging pawl catchers, numeral 18a indicates engaging pawls, numeral 8a indicates a printed circuit and numeral 8b indicates a support plate.

The input terminals 16, 17 are also used as rivet means for securing the battery case 18 to the sheet electrode 2.

[Sheet Electrode]

The sheet electrode 2 comprises, as shown in FIGS. 4, 9, 11 and 12, a sheet body 20, a pair of left and right electrode portions 21, 22 formed in the bottom surface of the sheet body 20, a battery case 18 provided at the left-side central portion on the surface of the sheet body 20, and a battery D which is replaceably stored in the battery case 18.

As shown in FIG. 3, the sheet body 20 has a rectangular shape wherein the sheet body 20 has an approximately the same width as the lateral width of the therapeutic device case 19 of a flattened rectangular shape and is made of the main body case 4 and the battery case 18, while having a longitudinal length approximately three times greater than the longitudinal length of the therapeutic device case 19.

The sheet body 20 can be made of a flexible and electrically insulating material such as polyurethane, vinyl chloride, polyester, or a laminar structure of polyester and polyvinyl chloride.

Figure 4:
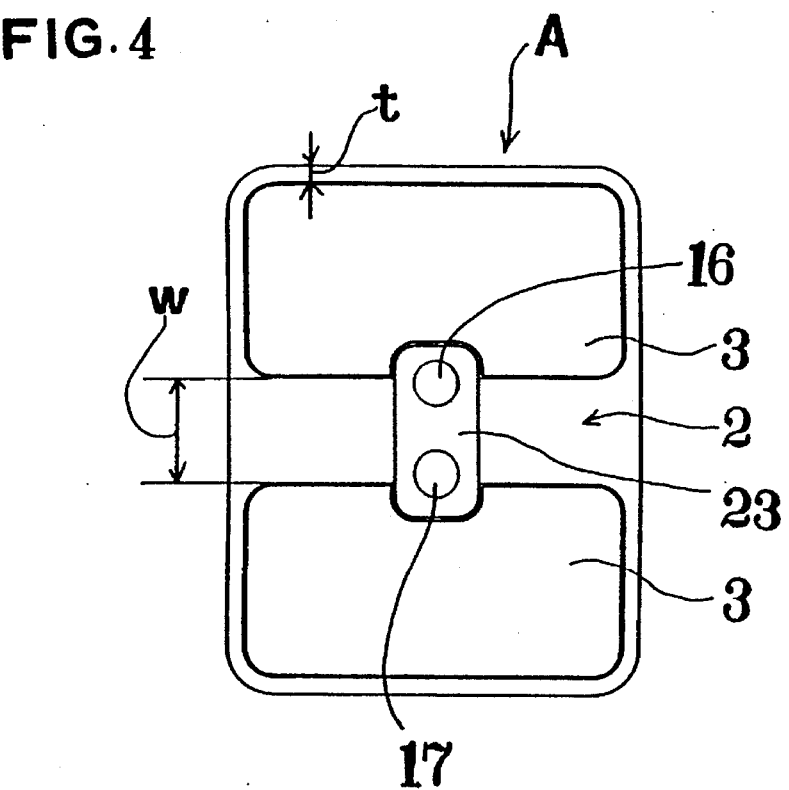
FIG. 4 is a bottom view of the low-frequency therapeutic device.

As shown in FIG. 4, a pair of left and right electrode portions 21, 22 are formed as thin rectangular membranes at the front and rear portion of the surface of the sheet body 20 with a predetermined space w therebetween in a longitudinal direction. The electrode portions 21, 22 are, for example, formed in such a manner that the electrode portions 21, 22 include carbon or silver therein or an electrically conductive ink is printed to produce a pattern.

These electrode portions 21, 22, as shown in FIG. 11, are connected with the above-mentioned input terminals 16, 17 so that output pulse generated by the output circuit 11 of the therapeutic device main body 1 is transmitted to the electrode portions 21, 22 by way of the input terminals 16, 17 through the output terminals 14, 15.

In FIGS. 2, 4, 11 and 12, numeral 23 indicates a semi-transparent electrically insulating cover, and the cover 23 covers the input terminals 16, 17 to assure insulation between the input terminals 16, 17 and a human body. The insulating cover 23 can be, for example, made of polyester or polyvinyl chloride.

As shown in FIGS. 9 and 12, the battery case 18 is provided with a battery mounting member 18b for replaceably mounting the battery D while forming a pair of slide engaging members 18c at the front and rear side portions thereof and the battery case 18 is slidably mounted on or dismounted from the main body case 4 by engaging the slide engaging members 18c with the slide engaging members 4a of the main body case 4.

The battery case 18 and the main case 4 are made of ABS resin.

As the battery D, for example, a button-like battery, a sheet-like battery, a coin-like battery, a cylindrical battery or a bottle-like battery with a voltage of 1.5 to 3.0 V can be used.

[Adhesive Pad]

As shown in FIGS. 2, 4, 11 and 12, the adhesive pad 3 is formed in a thin plate having the same shape as the above-mentioned electrodes 21, 22. An upper surface of the adhesive pad 3 is replaceably spread on the electrodes 21, 22, and a lower surface thereof can be adhered to the human skin. The adhesive pad 3 can also transmit output pulses generated by the respective electrodes 21, 22 to the human body.

The adhesive pad 3 may preferably be made of an adhesive pad having a favorable electric conductivity such as polyacrylic acid, polyacrylic salt, polyacrylic crosslinking compound, isobutylene-maleic anhydride copolymer and the like as inevitable constituents and preferably tackifier made of polyhydric alcohol such as glycerine, propylene glycol, polypropylene glycol, ethylene glycol, diethylene glycol, triethylene glycol, polyethylene glycol, and an electrolytic substance such as polyhydric sodium or potassium chloride, and a pH controlling agent such as sodium hydroxide, potassium hydroxide or organic amine, and a water, and flexibility adding agent.

The adhesive pad 3 has a thickness of 0.3 to 5 mm preferably 0.5 to 2 mm in view of the readiness of replacing it with a new adhesive pad when the sealing and adhering properties of the adhesive pad 3 deteriorates.

[Manner of Operation]

Figure 13:
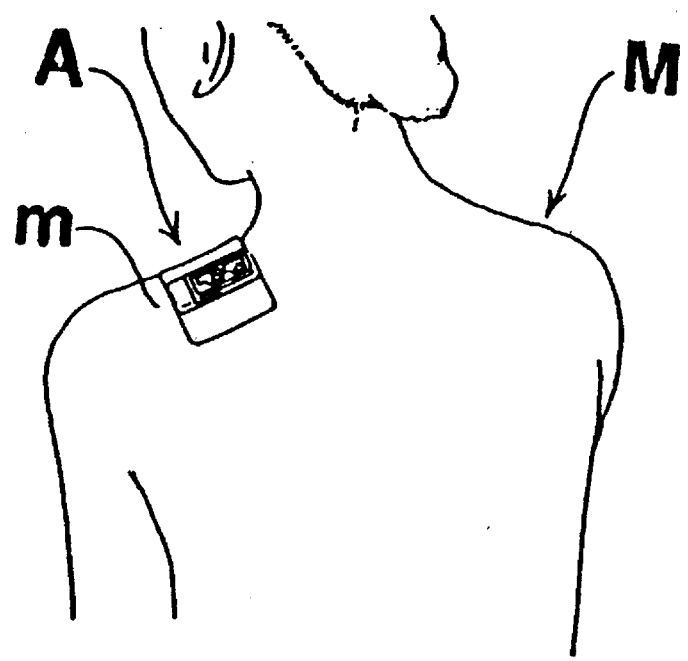
FIG. 13 is an explanatory view showing the manner of the operation of the low-frequency therapeutic device.
Figure 14:
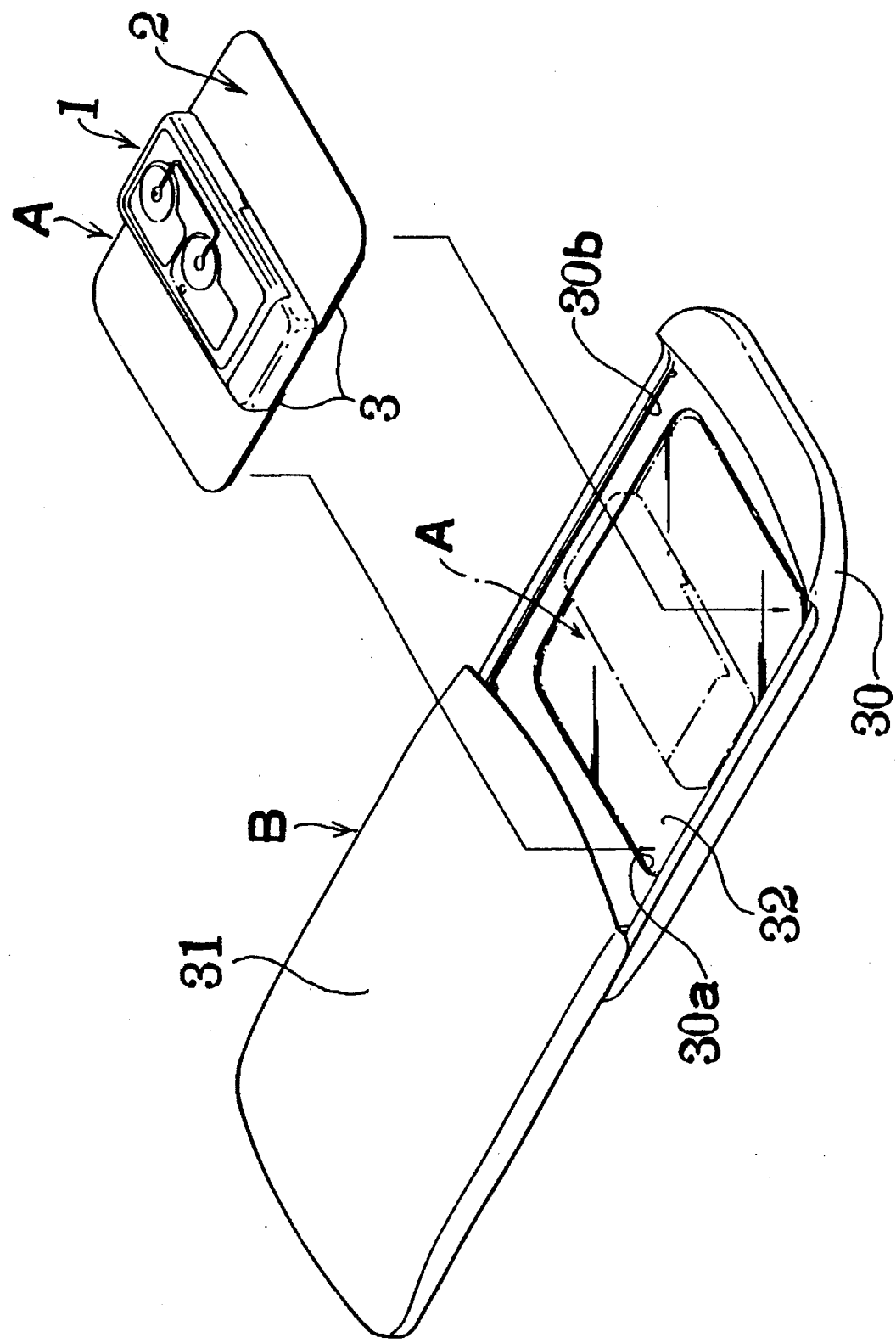
FIG. 14 is an explanatory view showing the manner of handling a therapeutic device storing case.
Figure 15:
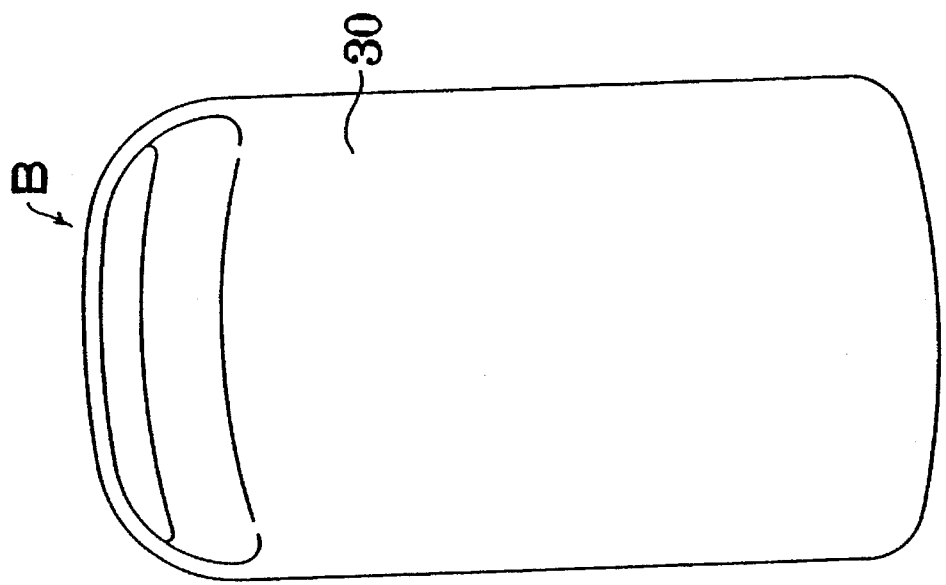
FIG. 15 is a plan view of the therapeutic device storing case.
Figure 16:
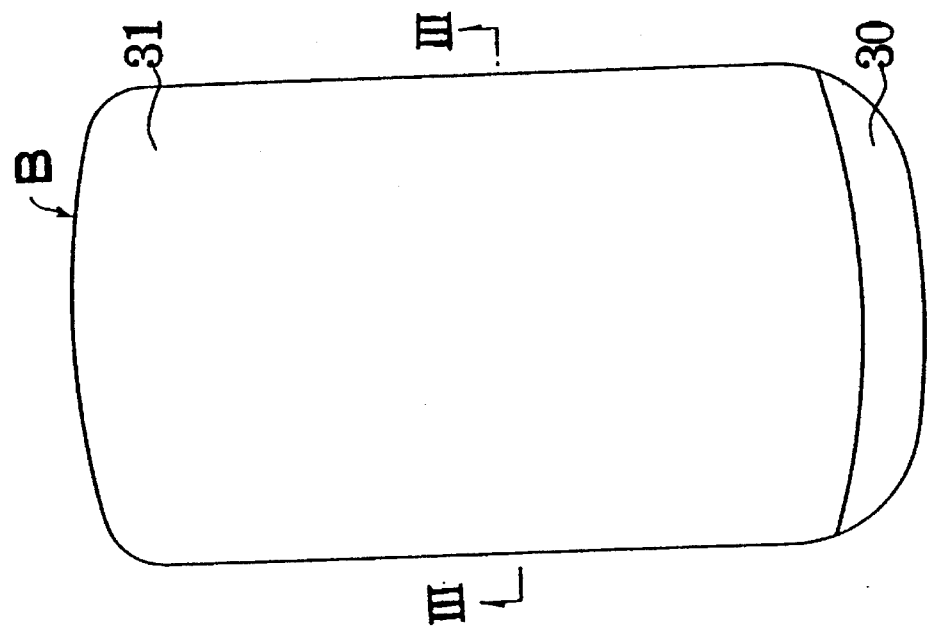
FIG. 16 is a bottom view of the therapeutic device storing case.
Figure 17:
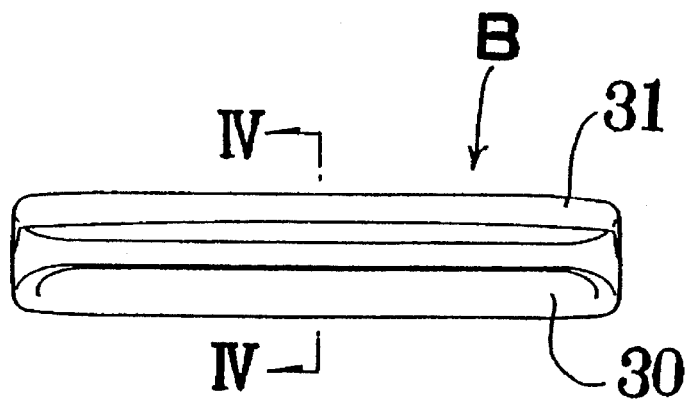
FIG. 17 is a front elevational view of the therapeutic device storing case.
Figure 18:
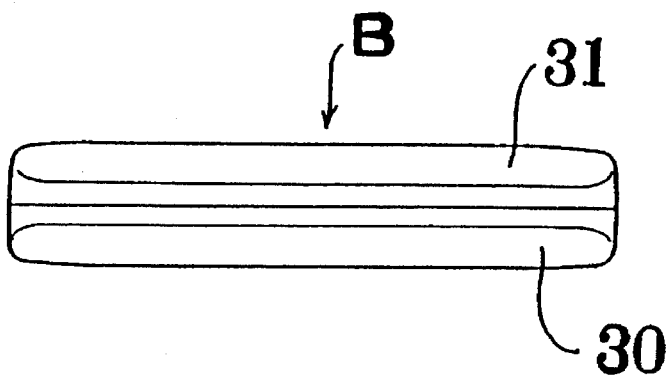
FIG. 18 is a rear elevational view of the therapeutic device storing case.
Figure 19:
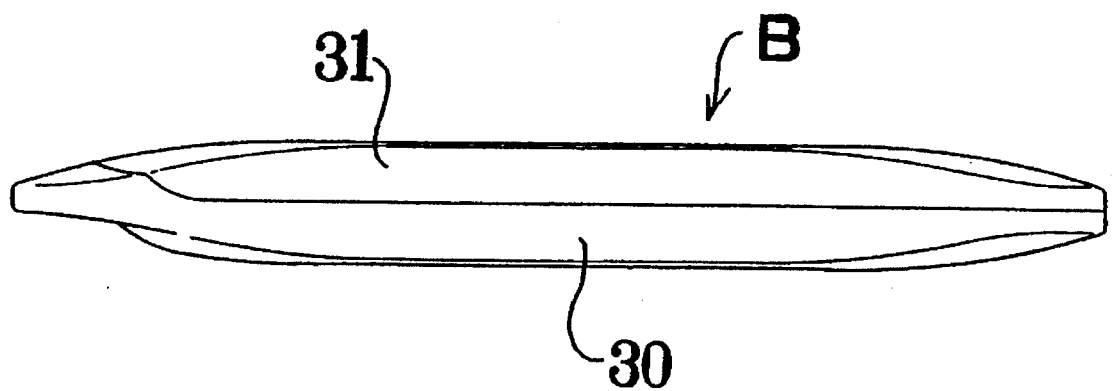
FIG. 19 is a right-side elevational view of the therapeutic device storing case.
Figure 20:
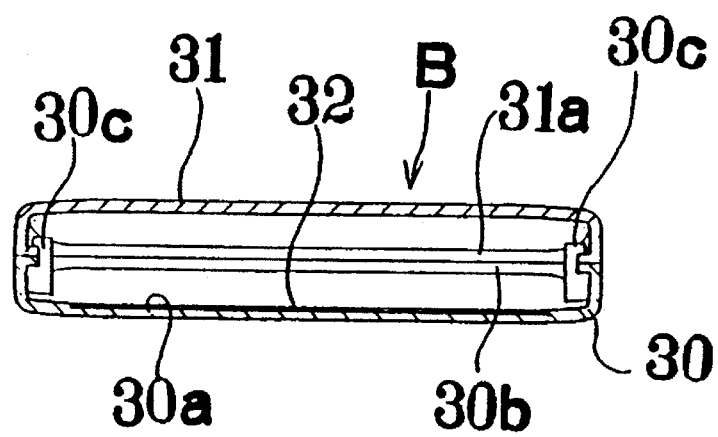
FIG. 20 is a cross-sectional view of the therapeutic device storing case taken along a line III—III of FIG. 15.
Figure 21:
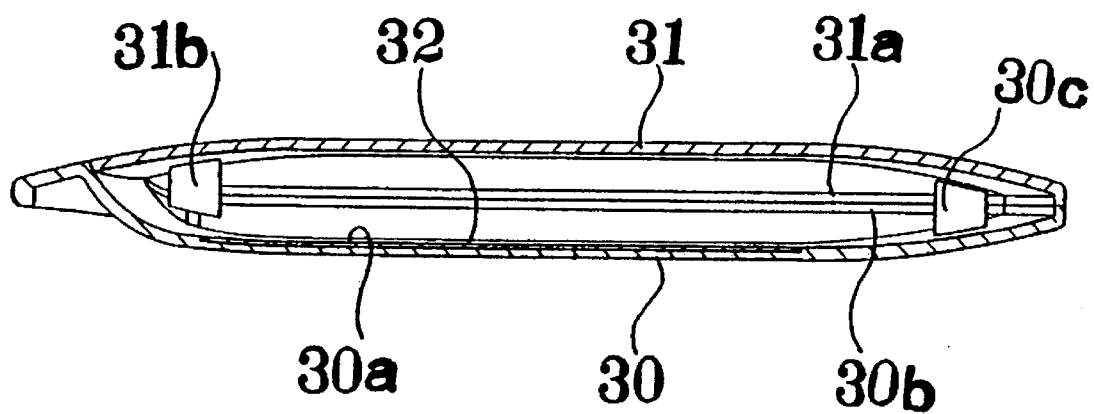
FIG. 21 is a cross-sectional view of the therapeutic device storing case taken along a line IV—IV of FIG. 17.
Figure 22:
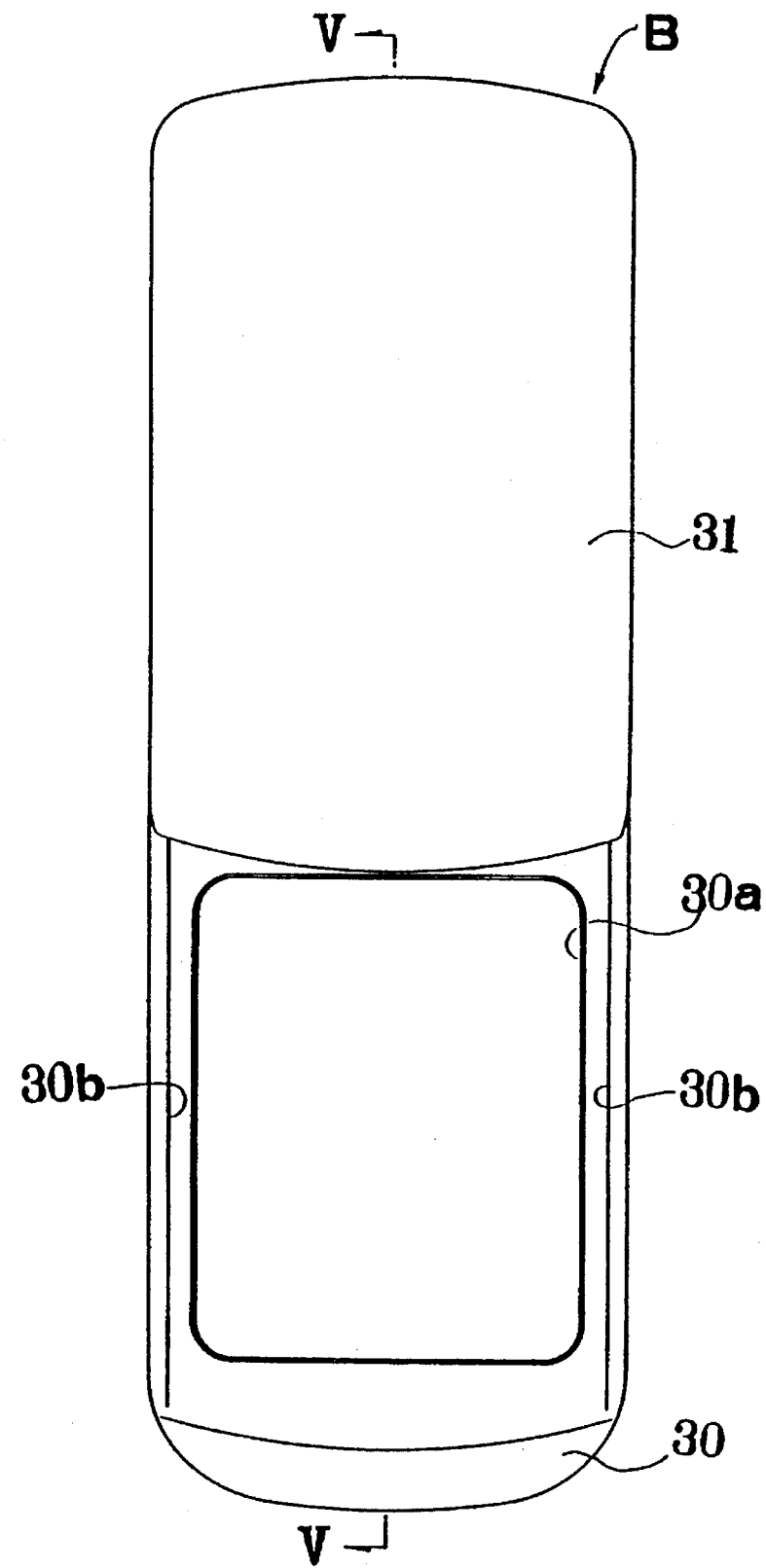
FIG. 22 is a plan view of the therapeutic device storing case in a lid-opened condition.

(1) The low-frequency therapeutic device A is taken out from the therapeutic device storing case B and, as shown in FIG. 13, the sheet electrode 2 of the low-frequency therapeutic device A is adhered to an affected part m of a human body M by way of the adhesive pad 3.

(2) The low-frequency output means 8 is operated by pressing the ON/UP switch 5. Since the display portion 7 is lit, the user can confirm with his eyes that the low-frequency output means 8 is being opera ted.

(3) When the ON/UP switch 5 is pressed, the output level is raised step by step, while, when the DOWN switch 6 is pressed, the output level is lowered step by step so that the output level can be adjusted at a desired level which gives each user comfort.

In this manner, corresponding to the taste or preference of the user, the above-mentioned seven types of modes, which comprise ① the tapping mode, ② the vibrating mode, ③ the continuous tapping mode, ④ the massaging mode, ⑤ the relaxing mode, ⑥ the massaging mode and ⑦ tapping mode are continuously and sequentially reproduced by means of the timer.

When all of the above-mentioned modes are over, the supply of the output is automatically stopped by means of the timer.

(4) The low-frequency therapeutic device A is removed from the human body by peeling off the sheet electrode 2 from the affected part m of the human body M.

(5) The low-frequency therapeutic device A is stored in the therapeutic device storing case B.

The sheet electrode 2 may be removed from the therapeutic main body 1 and the therapeutic main body 1 (see FIG. 9) can be stored in another storing case apart from the sheet electrode 2.

When the therapeutic device main body 1 is stored in the storing case separately; the therapeutic device main body 1 must be engaged with the sheet electrode 2 to assemble the low-frequency therapeutic device.

Such an assembling operation can be carried out by slidably engaging and mounting the slide engaging member 18b of the battery case 18 on the slide engaging member 4a of the main body case 4.

[Therapeutic device storing case]

In FIGS. 14 to 24, the therapeutic device storing case B stores the low-frequency therapeutic device A according to the above-mentioned present invention.

The therapeutic device storing case B is made of a case main body 30 and a slidable lid 31 and is formed as a flattened rectangular plate which have their respective central portions carved out. The therapeutic device storing case B is provided with a shouldered recess 30a, which has approximately the same shape as that of the sheet main body 20 of the sheet electrode 2, on the inner face of the case main body 30. An adhesive sheet 32 is fitted in the shouldered recess 30a, while, the surface of the adhesive sheet 32 is employed as a sheet electrode adhering surface and the sheet main body 20 of the sheet electrode 2 is peelably or replaceably adhered to the sheet electrode adhering surface so as to complete the storing of the low-frequency therapeutic device A in the therapeutic device storing case B.

For using the low-frequency therapeutic device A, the sheet electrode 2 is peeled off from the adhesive sheet 32 and is taken out of the therapeutic device storing case B. Numeral 30b indicates a slide guide portion, numeral 30c indicates a stopper receiving portion, numeral 31a indicates a slide engaging member which is slidably engaged with the slide guide portion 30b, and numeral 31b indicates a stopper.

[Other Embodiment]

Figure 25:
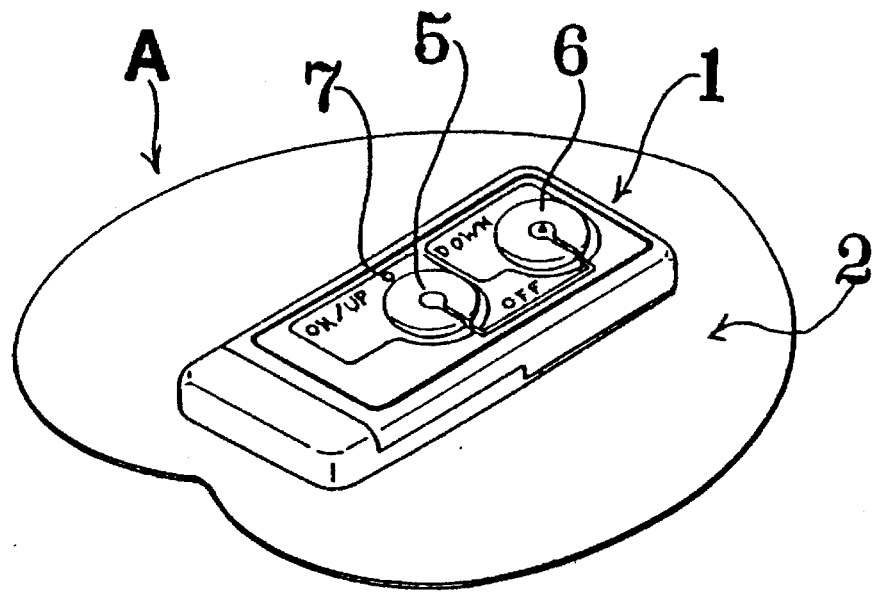
FIG. 25 is a perspective view of a low-frequency therapeutic device of a second embodiment showing an upper portion thereof.
Figure 26:
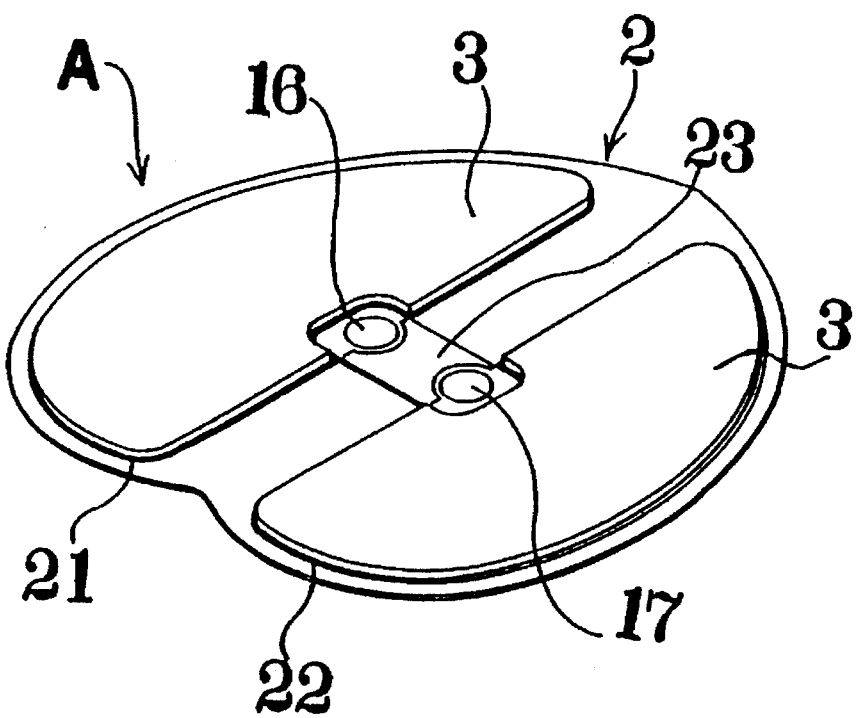
FIG. 26 is a perspective view of the low-frequency therapeutic device of the second embodiment showing a lower portion thereof.

FIGS. 25 and 26 show a low-frequency therapeutic device A of the second embodiment, wherein the sheet main body 20 of the sheet electrode 2 is formed in a charming heart shape so as to attract a lady's mind.

Figure 27:
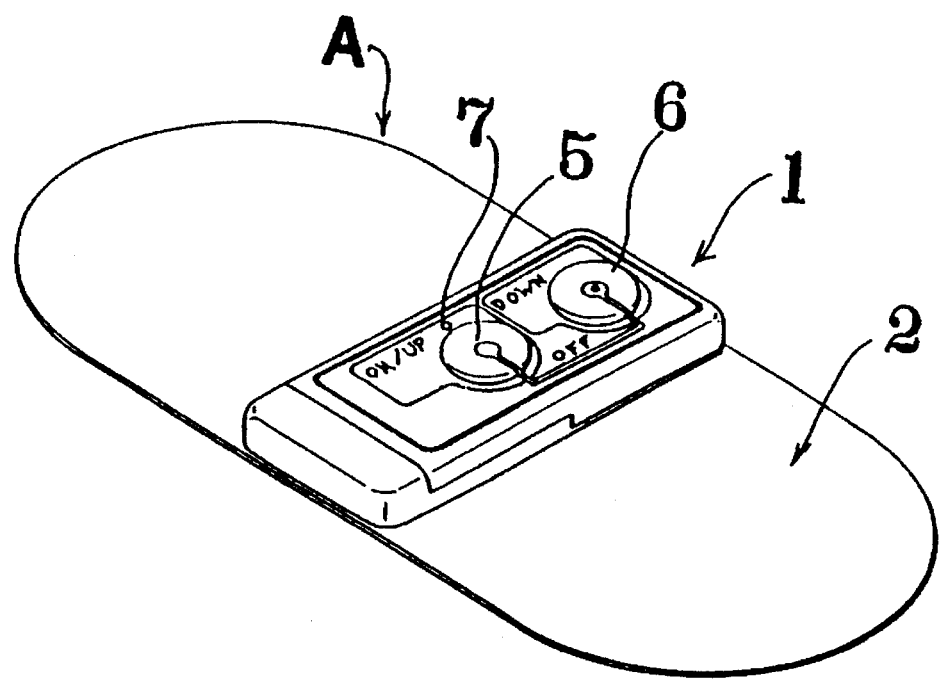
FIG. 27 is a perspective view of a low-frequency therapeutic device of a third embodiment showing an upper portion thereof.
Figure 28:
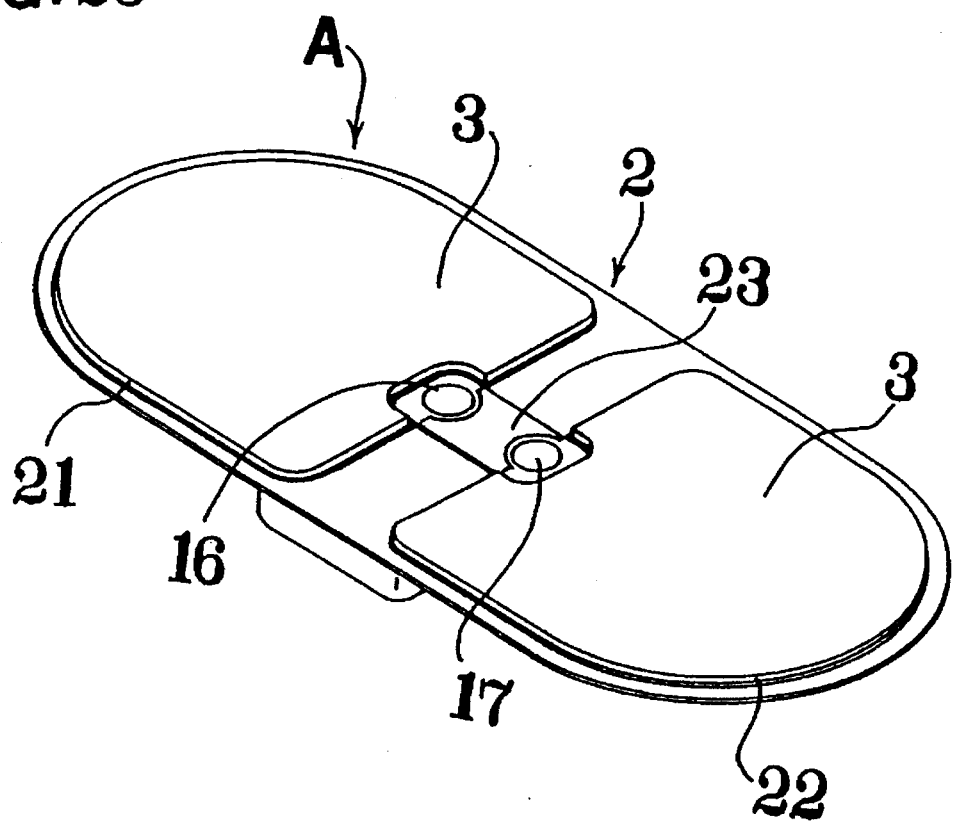
FIG. 28 is a perspective view of the low-frequency therapeutic device of the third embodiment showing a lower portion thereof.

FIGS. 27 and 28 show the low-frequency therapeutic device A of a third embodiment, wherein the sheet main body 20 of the sheet electrode 2 is formed in an elliptical shape with rounded peripheries.

Figure 29:
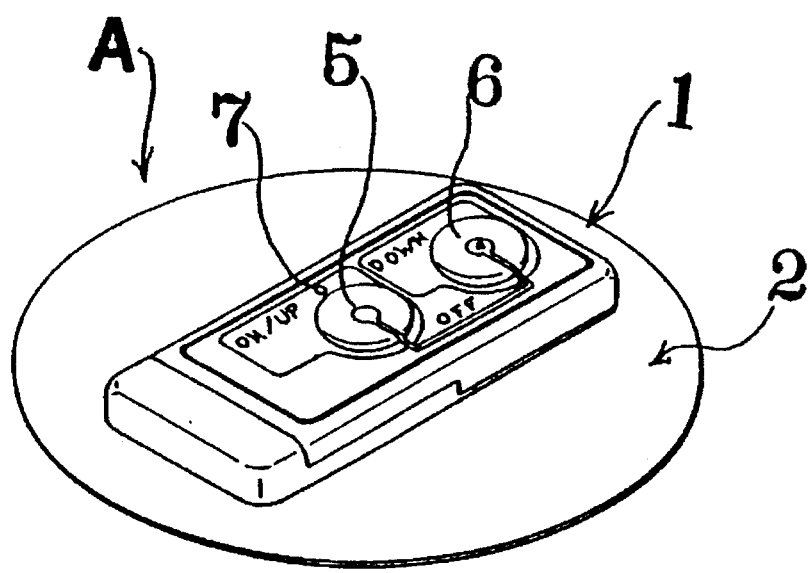
FIG. 29 is a perspective view of a low-frequency therapeutic device of a fourth embodiment showing an upper portion thereof.
Figure 30:
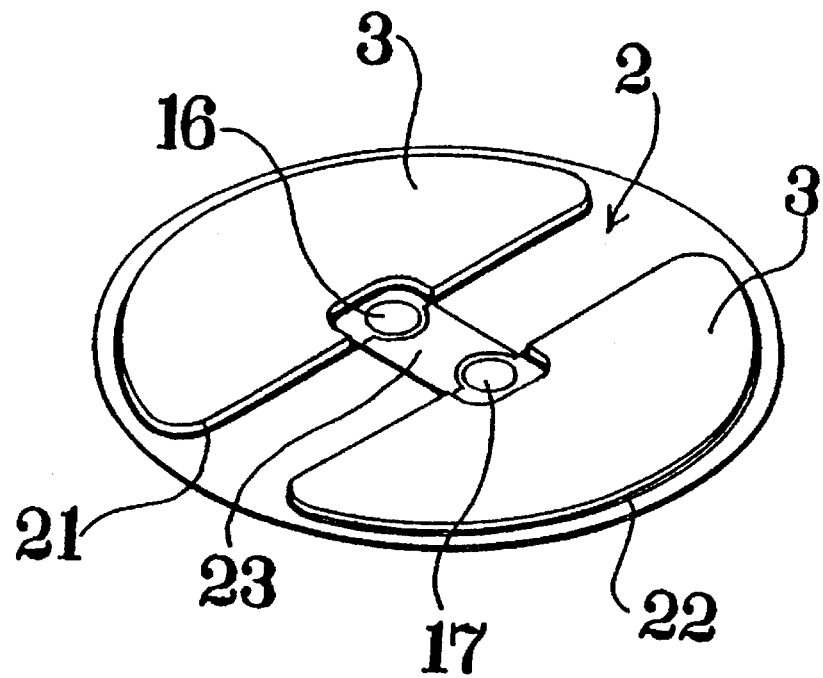
FIG. 30 is a perspective view of the low-frequency therapeutic device of the fourth embodiment showing a lower portion thereof.

FIGS. 29 and 30 show the low-frequency therapeutic device A of a fourth embodiment, wherein the sheet main body 20 of the sheet electrode 2 is formed in a circular shape so as to appear to have a soft image.

INDUSTRIAL APPLICABILITY

According to the present invention, the following advantages are obtained.

① The sheet electrode is made of a resilient or flexible sheet and has an area wider than that of the bottom surface of the therapeutic device main body so that the sheet electrode exhibits a favorable adhesiveness to the human skin thus assuring a favorable low-frequency therapeutic effect.

② Since the sheet electrode has a wide surface area, the sheet electrode can be adhered to a stiffened body part without considering the position of sweet spots, thus, providing a comfortable and effective therapy while facilitating the handling thereof.

③ The therapeutic device main body, the sheet electrode and the adhesive pad are replaceable from each other so that either one of them which requires replacement, can be selectively replaced thus, minimizing the maintenance fee.

④ plurality of operation modes which are different from each other are sequentially carried out at a predetermined interval so that it becomes possible to give various stimulus to the nerves of the affected part of a user thus promoting the therapeutic effect.

⑤ By merely turning on a start switch, the above mentioned operation modes are automatically and sequentially carried out so that the manner of operation is simplified and the device can be easily manipulated by the user.

⑥ The therapeutic device main body can be stored in the therapeutic device storing case when the device is not used and can be readily carried in such a stored form.

What is claimed is:

1. A low-frequency therapeutic device comprising a therapeutic device main body including means for generating a low-frequency pulse output disposed therein, a sheet electrode having a flexible sheet body and a battery case fixed thereto, said battery case being replaceably mounted on the therapeutic device main body, and means for attaching the sheet electrode to a surface.

2. A low-frequency therapeutic device according to claim 1, wherein the means for generating comprises a control unit, the control unit having programmed therein a plurality of modes which are different in periods of generating low-frequency electric pulses and which are output continuously and in sequence by a single switching operation.

3. A low-frequency therapeutic device according to claim 1, wherein the means for attaching the sheet electrode to a surface includes at least one adhesive pad removably adhered to the sheet electrode.

4. A therapeutic device kit, comprising:

a low-frequency therapeutic device including a main body and a flexible sheet electrode attached thereto, the flexible sheet electrode being adhesively attachable to a surface; and a therapeutic device storage case including a case main body having a sheet electrode adhering surface inside thereof for adhering the sheet electrode of the low-frequency therapeutic device thereto;

the therapeutic device storage case further including a lid having means for slidably coupling to the case main body to permit reception of the therapeutic device within the therapeutic storage case when opened, and for enclosing the therapeutic device therein when closed.

5. A low-frequency therapeutic device comprising:

a therapeutic device main body including means for producing a low-frequency pulse output disposed therein;

a sheet electrode replaceably mounted on the therapeutic device main body, the sheet electrode and the therapeutic device main body being slidably engaged; and at least one adhesive pad replaceably mounted on the sheet electrode.

6. A low-frequency therapeutic device, comprising:

a sheet electrode including a flexible sheet body having an upper and lower surface, said sheet electrode further including a pair of electrode portions formed on said lower surface of said flexible sheet body;

a therapeutic device case including a battery case and a main body case, said battery case being fixed to said upper surface of said flexible sheet body, said main body case being removably connectable to said battery case, said flexible sheet body extending beyond opposed sides of said therapeutic device case to permit conformable application of said flexible sheet body on an exterior body portion of an individual; and means for generating a low-frequency pulse disposed within said therapeutic device case and having an output connected to said electrode portions.

7. A low-frequency therapeutic device according to claim 6, further comprising at least one adhesive pad replaceably mounted on said sheet electrode.

8. A low-frequency therapeutic device according to claim 7, wherein said at least one adhesive pad is made of at least one of polyacrylic acid, polyacrylic salt, polyacrylic cross-linking compound, and isobutylene-maleic anhydride copolymer.

9. A low-frequency therapeutic device according to claim 7, wherein said at least one adhesive pad has a thickness in a range between about 0.3 mm and about 5 mm.

10. A low-frequency therapeutic device according to claim 9, wherein said thickness is in a range between about 0.5 mm and about 2 mm.

11. A low-frequency therapeutic device according to claim 6, further comprising means for halting said output responsive to a malfunction of said low-frequency therapeutic device and for limiting said output to a maximum current value.

12. A low-frequency therapeutic device according to claim 11 wherein said means for generating includes a booster circuit having an inductor and a condenser, and said means for halting and limiting including means for discharging said condenser in the event of malfunction.

13. A low-frequency therapeutic device according to claim 11, wherein said maximum current value is 20 mA.

14. A low-frequency therapeutic device according to claim 6, wherein said flexible sheet body is made of one of polyurethane, vinyl chloride, polyester, and a laminar structure of polyester and polyvinyl chloride.

15. A low-frequency therapeutic device according to claim 6, wherein said therapeutic device case is substantially the same width as said flexible sheet body, and said sheet body is approximately three times longer than a length of said therapeutic device case, and said therapeutic device case being substantially centrally disposed on said flexible sheet body.

* * * * *